US010611848B2

(12) United States Patent
Le Doussal et al.

(10) Patent No.: US 10,611,848 B2
(45) Date of Patent: *Apr. 7, 2020

(54) ANTIBODY AGAINST GD2-O-ACETYLATED GANGLIOSIDE WITH PRO-APOPTOTIC ACTIVITY

(71) Applicants: OGD2 PHARMA, Nantes (FR); UNIVERSITE DE NANTES, Nantes (FR)

(72) Inventors: Jean-Marc Le Doussal, Lausanne (CH); Mickael Terme, Nantes (FR); Mylene Dorvillius, Nantes (FR)

(73) Assignees: OGD2 PHARMA, Nantes (FR); UNIVERSITE DE NANTES, Nantes (FR)

(*) Notice: Subject to any disclaimer, the term of this patent is extended or adjusted under 35 U.S.C. 154(b) by 382 days.

This patent is subject to a terminal disclaimer.

(21) Appl. No.: 15/035,979

(22) PCT Filed: Nov. 11, 2014

(86) PCT No.: PCT/EP2014/003009
§ 371 (c)(1),
(2) Date: May 11, 2016

(87) PCT Pub. No.: WO2015/067375
PCT Pub. Date: May 14, 2015

(65) Prior Publication Data
US 2016/0272722 A1    Sep. 22, 2016

(30) Foreign Application Priority Data
Nov. 11, 2013 (EP) ................................ 13005298

(51) Int. Cl.
*C07K 16/30* (2006.01)
*A61K 39/00* (2006.01)

(52) U.S. Cl.
CPC ...... *C07K 16/3084* (2013.01); *C07K 16/3015* (2013.01); *C07K 16/3023* (2013.01); *A61K 2039/505* (2013.01); *C07K 2317/24* (2013.01); *C07K 2317/52* (2013.01); *C07K 2317/522* (2013.01); *C07K 2317/524* (2013.01); *C07K 2317/526* (2013.01); *C07K 2317/53* (2013.01); *C07K 2317/565* (2013.01); *C07K 2317/72* (2013.01); *C07K 2317/73* (2013.01); *C07K 2317/76* (2013.01); *C07K 2317/92* (2013.01)

(58) Field of Classification Search
None
See application file for complete search history.

(56) References Cited

U.S. PATENT DOCUMENTS

| 5,225,539 A | 7/1993 | Winter |  |
|---|---|---|---|
| 5,585,089 A | 12/1996 | Queen et al. |  |
| 2009/0191221 A1* | 7/2009 | Lin | C07K 16/2896 424/174.1 |
| 2010/0150910 A1 | 6/2010 | Birkle et al. |  |
| 2011/0033378 A1* | 2/2011 | Dimasi | A61K 47/48215 424/1.49 |
| 2012/0164137 A1* | 6/2012 | Sass | C07K 16/00 424/133.1 |
| 2012/0264137 A1* | 10/2012 | Vanjari | C12M 47/06 435/7.1 |

FOREIGN PATENT DOCUMENTS

GB    2 188 638 A    10/1987

OTHER PUBLICATIONS

Natsume et al (CR, 68(10):3863-3872, 2008).*
Dorai et al (MI, 29(12):1487-1491, 1992).*
Alvarez-Rueda, Nidia, et al: "A Monoclonal Antibody to O-Acetyl-GD2 Ganglioside and Not to GD2 Shows Potent Anti-Tumor Activity without Peripheral Nervous System Cross-Reactivity", PLOS One, vol. 6, No. 9, Sep. 22, 2011 (Sep. 22, 2011), p. e25220, XP055107662, DOI: 10.1371/journal.pone.0025220.
Natsume, Akito, et al: "Engineered Antibodies of IgG1/IgG3 Mixed Isotype with Enhanced Cytotoxic Activities", Cancer Research, American Association for Cancer Research, US, vol. 68, No. 10, May 15, 2008 (May 15, 2008), pp. 3863-3872, XP007913550, ISSN: 0008-5472, DOI: 10.1158/0008-5472.CAN-07-6297.
Cochonneau, Denis, et al: "Cell cycle arrest and apoptosis induced by O-acetyl-GD2-specific monoclonal antibody 8B6 inhibits tumor growth in vitro and in vivo", Cancer Letters, New York, NY, US, vol. 333, No. 2, Jan. 28, 2013 (Jan. 28, 2013), pp. 194-204, XP028581871, ISSN: 0304-3835, DOI: 10.1016/J.CANLET.2013.01.032.
Alvarez-Rueda, Nidia, et al: "Binding activities and antitumor properties of a new mouse/human chimeric antibody specific for GD2 ganglioside antigen", Clinical Cancer Research, The American Association or Cancer Research, US, vol. 13, No. 18 Pt 2, Sep. 15, 2007 (Sep. 15, 2007), pp. 5613s-5620s, XP002550652, ISSN: 1078-0432, DOI: 10.1158/1078-0432.CCR-07-1057.
International Search Report, dated Mar. 2, 2015, from corresponding PCT Application.

* cited by examiner

Primary Examiner — Brad Duffy
(74) Attorney, Agent, or Firm — Young & Thompson

(57) ABSTRACT

Antibody which binds to the O-acetylated-GD2 ganglioside, includes: a) a light chain including three light chain complementary regions (CDRs) having the following amino acid sequences: CDR1: QSLLKNNGNTFL (SEQ id no 1), CDR2: KVS, CDR3: SQSTHIPYT (SEQ id no 2); and a light chain framework sequence from an immunoglobulin light chain, including the human kappa (κ)CL domain; and b) a heavy chain including three heavy chain complementary regions (CDRs) having the following amino acid sequences: CDR1: EFTFTDYY (SEQ id no 3), CDR2: IRNRANGYTT (SEQ id no 4), CDR3: ARVSNWAFDY (SEQ id no 5), and a heavy chain framework sequence from an immunoglobulin heavy chain, including CH2 and CH3 domains from a human IgG1, and a CH1 domain from a human IgG1, which is mutated to restore pairing between CH1 and light chain that is typical of other human IgG subclasses or substituted by a CH1 domain from such non-IgG1 subclasses as human IgG2, IgG3 or IgG4.

23 Claims, 5 Drawing Sheets
Specification includes a Sequence Listing.

Light chain sequence:

```
  VL              20              *              40                              60
DVVMTQTPLS LPVSLGDQAS ISCRSSQSLL KNNGNTFLHW YLQKSGQSPK LLIYKVSNRL
           80              100        *                              Cκ     120
SGVPDRFSGS GSGTYFTLKI SRVEAEDLGV YFCSQSTHIP YTFGGGTKLE IKRTVAAPSV
           140      *           160                                          180
FIFPPSDEQL KSGTASVVCL LNNFYPREAK VQWKVDNALQ SGNSQESVTE QDSKDSTYSL
           200    *
SSTLTLSKAD YEKHKVYACE VTHQGLSSPV TKSFNRGEC
```

Heavy chain sequence:

```
  VH              20      *              40                                  60
EVKLVESGGG LVLPGDSLRL SCATSEFTFT DYYMTWVRQP PRKALEWLGF IRNRANGYTT
           80              100   *                                   CH1    120
EYNPSVKGRF TISRDNSQSI LYLQMNTLRT EDSATYYCAR VSNWAFDYWG QGTTLTVSSA
           140     *            160                                          180
STKGPSVFPL APSSKSTSGG TAALGCLVKD YFPEPVTVSW NSGALTSGVH TFPAVLQSSG
           200   *           220  Hinge                         CH2         240
LYSLSSVVTV PSSSLGTQTY ICNVNHKPSN TKVDKKVEPK SCDKTHTCPP CPAPELLGGP
           260    *           280                                            300
SVFLFPPKPK DTLMISRTPE VTCVVVDVSH EDPEVKFNWY VDGVEVHNAK TKPREEQYNS
           320     *           340          CH3                              360
TYRVVSVLTV LHQDWLNGKE YKCKVSNKAL PAPIEKTISK AKGQPREPQV YTLPPSREEM
           380 *              400                                            420
TKNQVSLTCL VKGFYPSDIA VEWESNGQPE NNYKTTPPVL DSDGSFFLYS KLTVDKSRWQ
       *   440
QGNVFSCSVM HEALHNHYTQ KSLSLSPGK
```

Figure 1

ASTKGPSVFP LAPCSKSTSG GTAALGCLVK DYFPEPVTVS WNSGALTSGV HTFPAVLQSS
GLYSLSSVVT VPSSSLGTQT YICNVNHKPS NTKVDKKV EPKSCDKTHTCPPCP APELLGGP

Figure 2

ASTKGPSVFP LAPCSKSTSG GTAALGCLVK DYFPEPVTVS WNSGALTSGV HTFPAVLQSS
GLYSLSSVVT VPSSSLGTQT YICNVNHKPS NTKVDKKV EPKS<u>S</u>DKTHTCPPC PAPELLGGP

Figure 3

ASTKGPSVFP LAPCSRSTSG GTAALGCLVK DYFPEPVTVS WNSGALTSGV HTFPAVLQSS
GLYSLSSVVT VPSSSLGTQT YTCNVNHKPS NTKVDKRV EPKSCDKTHTCPPCP APELLGGP

Figure 4

ASTKGPSVFP LAPCSKSTSG GTAALGCLVK DYFPEPVTVS WNSGALTSGV HTFPAVLQSS
GLYSLSSVVT VPSSSLGTQT YICNVNHKPS NTKVDKKV ELKTPLGDTTHT CPRCP
EPKSCDTPPPCPRCP EPKSCDTPPPCPRCP EPKSCDTPPPCPRCP APELLGGP

Figure 5

ASTKGPSVFP LAPCSRSTSG GTAALGCLVK DYFPEPVTVS WNSGALTSGV HTFPAVLQSS
GLYSLSSVVT VPSSSLGTQT YTCNVNHKPS NTKVDKRV ELKTPLGDTTHT
CPRCP EPKSCDTPPPCPRCP EPKSCDTPPPCPRCP EPKSCDTPPPCPRCP APELLGGP

Figure 6

ASTKGPSVFP LAPCSKSTSG GTAALGCLVK DYFPEPVTVS WNSGALTSGV HTFPAVLQSS
GLYSLSSVVT VPSSSLGTQT YICNVNHKPS NTKVDKKV ELKTPLGDTTHT CPRCP
APELLGGP

Figure 7

ASTKGPSVFP LAPCSRSTSG GTAALGCLVK DYFPEPVTVS WNSGALTSGV HTFPAVLQSS
GLYSLSSVVT VPSSSLGTQT YTCNVNHKPS NTKVDKRV ELKTPLGDTTHT CPRCP
APELLGGP

Figure 8

ASTKGPSVFP LAPCSRSTSG GTAALGCLVK DYFPEPVTVS WNSGALTSGV HTFPAVLQSS
GLYSLSSVVT VPSSSLGTQT YTCNVNHKPS NTKVDKRV EPKSSDKTHT CPPCP

Figure 9

ASTKGPSVFP LAPCSRSTSE STAALGCLVK DYFPEPVTVS WNSGALTSGV HTFPAVLQSS GLYSLSSVVT
VPSSNFGTQT YTCNVDHKPS NTKVDKTV EPKSCDKTHT CPPCP

Figure 10

ASTKGPSVFP LAPCSRSTSE STAALGCLVK DYFPEPVTVS WNSGALTSGV HTFPAVLQSS GLYSLSSVVT
VPSSSLGTKT YTCNVDHKPS NTKVDKRV EPKSCDKTHT CPPCP

Figure 11

ANTIBODY AGAINST GD2-O-ACETYLATED GANGLIOSIDE WITH PRO-APOPTOTIC ACTIVITY

The present International patent application claims the priority of the European patent application EP 13005298.8 filed on Nov. 11, 2013, which is herein incorporated by reference.

FIELD OF THE INVENTION

The present invention provides novel antibodies and their uses in cancer therapies.

BACKGROUND OF THE INVENTION

It has been previously demonstrated that cancers of neuroectodermal origin specifically express the GD2-O-acetylated ganglioside and that a therapeutic antibody targeting GD2-O-acetylated ganglioside (mAb 8B6) can be administrated and show beneficial effects without neurotoxicity, especially due to the absence of expression of this cancer antigen on healthy cells, notably on peripheral nerves.

The potent activity of the anti-OAcGD2 murine IgG3,κ mAb 8B6 has been described in ALVAREZ-RUEDA et al. (*PLoS One*, vol. 6(9), p:e25220, 2011). This antibody has an efficient ADCC and CDC activity in vitro, and also shows a pro-apoptotic activity (COCHONNEALU et al., *Cancer Lett.*, vol. 333(2), p: 194-204, 2013). This antibody induces cell death by an apoptotic pathway corresponding to the inhibition of the proliferation for OAcGD2 positive tumor cells in culture via cell cycle arrest and apoptosis in vitro.

Passive immunotherapy performed with mAb 8B6 to OAcGD2 is effective in suppressing the growth of OAcGD2-expressing tumor in three animal models. It was demonstrated that lytic function of NK cells is not a requirement for the in vivo activity of mAb 8B6 (COCHONNEAU et al., above mentioned, 2013).

Now, to develop a humanized antibody the inventors have generated a human-mouse chimeric antibody, named c8B6 (IgG1, κ).

While this c8B6 antibody showed an in vivo activity comparable to that of in immuno-competent mice tumor models, a complete loss of pro-apoptotic activity compared to murine mAb 8B6 was observed in vitro. It was thus envisaged that the loss of pro-apoptotic activity of mAb c8B6 results from the loss of specific structures that differs between murine IgG3 and human IgG1.

Consequently, it was concluded that an IgG1 human chimerization can not be done for obtaining a valuable therapeutic.

SUMMARY OF THE INVENTION

Now, the inventors have surprisingly shown that a specific mutation in the CH1γ1 of c8B6 or its substitution by a CH1γ3 result in the restoration of the pro-apoptotic activity. Consequently, it seems that, in the c8B6, the pairing between the light chain and the heavy chain of the human IgG1—atypical due to the absence of cysteine near position 133 in the human CH1γ1 domain—is associated with the loss of pro-apoptotic activity for this antibody.

Thus, the obtained antibody comprises the good combination of IgG1 properties—i.e. ADCC activity and a long half-life—with a pro-apoptotic activity.

Consequently, the present invention relates to an antibody, or functional fragment thereof, recognizing the O-acetylated-GD2 ganglioside, said antibody comprising:

a) a light chain comprising three light chain complementary regions (CDRs) having the following amino acid sequences:
  i) the light chain CDR1: QSLLKNNGNTFL (SEQ id no 1);
  ii) the light chain CDR2: KVS;
  iii) the light chain CDR3: SQSTHIPYT (SEQ id no 2); and
  a light chain framework sequence from an immunoglobulin light chain, wherein said framework sequence comprises a human kappa (κ) CL domain; and b) a heavy chain comprising three heavy chain complementary regions (CDRs) having the following amino acid sequences:
  i) the heavy chain CDR1: EFTFTDYY (SEQ id no 3);
  ii) the heavy chain CDR2: IRNRANGYTT (SEQ id no 4);
  iii) the heavy chain CDR3: ARVSNWAFDY (SEQ id no 5); and
  a heavy chain framework sequence from an immunoglobulin heavy chain, wherein said framework sequence comprises:
   1) the CH2 and CH3 domains from a human IgG1, and
   2) a CH1 domain from a human IgG1, which is mutated so as to restore the pairing between the CH1 and the light chain typical of the other IgG subclasses, or is substituted with a CH1 domain from non-IgG1 subclasses, such as human IgG2, IgG3 or IgG4.

The present invention also relates to a pharmaceutical composition comprising at least one of such antibody, and a pharmaceutically acceptable carrier.

Additionally, the present invention relates to a method for treating a cancer comprising providing to a patient in need thereof such a pharmaceutical composition which comprises at least one said antibody, or at least one functional fragment thereof.

Additionally, the present invention relates to the use of at least one of such antibody, or of at least one functional fragment thereof for the preparation of a medicament for treating and/or preventing cancer.

Finally, the present invention relates to a method for increasing the therapeutic efficacy of human IgG1 antibody which binds specifically to the O-acetylated-GD2 ganglioside, derivative or a functional fragment thereof, comprising the step of mutating the human CH1γ1 domain from said antibody, so as to restore the pairing between CH1 and CL domains that is typical of other IgG subclasses, or by substituting said human CH1γ1 domain by the CH1 domain from a human IgG2 (CH1γ2), IgG3 (CH1γ3) or IgG4 (CH1γ4).

BRIEF DESCRIPTION OF THE FIGURES

FIG. 1 shows the light and heavy chain sequences of the c8B6 antibody.

FIG. 2 shows the CH1 and hinge domains sequence of the 301.14a antibody.

FIG. 3 shows the CH1 and hinge domains sequence of the 301.14b antibody.

FIG. 4 shows the CH1 and hinge domains sequence of the 301.15 antibody.

FIG. 5 shows the CH1 and hinge domains sequence of the 301.16 antibody.

FIG. 6 shows the CH1 and hinge domains sequence of the 301.17 antibody.

FIG. 7 shows the CH1 and hinge domains sequence of the 301.18 antibody.

FIG. 8 shows the CH1 and hinge domains sequence of the 301.19 antibody.

FIG. 9 shows the CH1 and hinge domains sequence of the 301.15b antibody.

FIG. 10 shows the CH1 and hinge domains sequence of the 301.20 antibody.

FIG. 11 shows the CH1 and hinge domains sequence of the 301.21 antibody.

DETAILED DESCRIPTION

Figure 12:
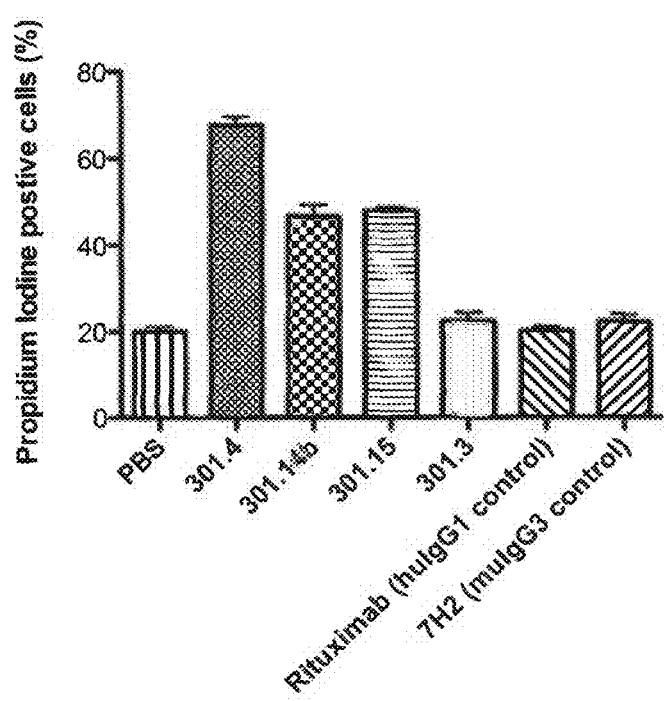
FIG. 12 shows the direct cytotoxicity of anti-OacGD2 antibodies by propidium iodine.

In a first aspect, the present invention concerns an antibody, or functional fragment thereof, which binds specifically to the O-acetylated-GD2 ganglioside, said antibody comprising:
  a) a light chain comprising three light chain complementary regions (CDRs) having the following amino acid sequences:
    i) the light chain CDR1: QSLLKNNGNTFL (SEQ id no 1),
    ii) the light chain CDR2: KVS;
    iii) the light chain CDR3: SQSTHIPYT (SEQ id no 2); and
    a light chain framework sequence from an immunoglobulin light chain, wherein said framework sequence comprises a human kappa (κ) CL domain; and
  b) a heavy chain comprising three heavy chain complementary regions (CDRs) having the following amino acid sequences:
    i) the heavy chain CDR1: EFTFTDYY (SEQ id no 3);
    ii) the heavy chain CDR2: IRNRANGYTT (SEQ id no 4);
    iii) the heavy chain CDR3: ARVSNWAFDY (SEQ id no 5); and
    a heavy chain framework sequence from an immunoglobulin heavy chain, wherein said framework sequence comprises:
    1) the CH2 and CH3 domains from a human IgG1, and
    2) a CH1 domain from a human IgG1, which is mutated so as to restore the IgG pairing between CH1 and light chain typical of the other IgG subclasses, or substituted with a CH1 domain from non-IgG subclass, such as human IgG2, IgG3 or IgG4.

Said antibody has a restored pro-apoptotic activity against cells expressing GD2-O-Acetylated ganglioside, while also exhibiting IgG1 properties as ADCC activity and half-life.

An antibody is an immunoglobulin molecule corresponding to a tetramer comprising four polypeptide chains, two identical heavy (H) chains (about 50-70 kDa when full length) and two identical light (L) chains (about 25 kDa when full length) inter-connected by disulfide bonds. Light chains are classified as kappa and lambda.

The heavy chain is classified as gamma for the IgG. Each heavy chain is comprised of a N-term heavy chain variable region (abbreviated herein as HCVR) and a heavy chain constant region. The heavy chain constant region is comprised of three domains (CH1, CH2, and CH3) for IgG, with a hinge domain between CH1 and CH2 domains.

Each light chain is comprised of a N-term light chain variable region (abbreviated herein as LCVR) and a light chain constant region. The light chain constant region is comprised of one domain, CL. The HCVR and LCVR regions can be further subdivided into regions of hypervariability, termed complementarity determining regions (CDRs), interspersed with regions that are more conserved, termed framework regions (FR). Each HCVR and LCVR is composed of three CDRs and four FRs, arranged from amino-terminus to carboxy-terminus in the following order: FR1, CDR1, FR2, CDR2, FR3, CDR3, FR4. The assignment of amino acids to each domain is in accordance with well-known conventions (IMGT, The International Immunogenetics Information System®, LEFRANC et al., *Nucleic Acids Research, vol. 27, p: 209-212, 1999*). The functional ability of the antibody to bind a particular antigen depends on the variable regions of each light/heavy chain pair, and is largely determined by the CDRs.

The term "functional fragments" as used herein refers to antibody fragments, which bind specifically to the O-acetylated-GD2 ganglioside and which comprise CH1 domain. Such fragments can be simply identified by the skilled person and comprise, as an example, $F_{ab}$ fragment (e.g., by papain digestion), $F_{ab}'$ fragment (e.g., by pepsin digestion and partial reduction), $F_{(ab')_2}$ fragment (e.g., by pepsin digestion), Fac (e.g., by plasmin digestion), and also $F_d$ (e.g., by pepsin digestion, partial reduction and re-aggregation) fragment are encompassed by the invention.

Such fragments can be produced by enzymatic cleavage, synthetic or recombinant techniques, as known in the art and/or as described herein. Antibodies can also be produced in a variety of truncated forms using antibody genes in which one or more stop codons have been introduced upstream of the natural stop site. For example, a combination gene encoding a $F_{(ab')_2}$ heavy chain portion can be designed to include DNA sequences encoding the $CH_1$ domain and/or hinge region of the heavy chain. The various portions of antibodies can be joined together chemically by conventional techniques, or can be prepared as a contiguous protein using genetic engineering techniques.

The expression "binding specifically to the O-acetylated-GD2 ganglioside" refers to a $K_D$ of less than $2 \times 10^{-7}$ M.

The term "antibody", as used herein, refers to a monoclonal antibody per se. A monoclonal antibody can be a human antibody, chimeric antibody and/or humanized antibody.

The antibodies useful in the invention are produced recombinantly, as manipulation of the typically murine or other non-human antibodies with the appropriate specificity is required in order to convert them to humanized form. Antibodies may or may not be glycosylated, though glycosylated antibodies are preferred. Antibodies are properly cross-linked via disulfide bonds, as is well-known.

According to a preferred embodiment, the antibody of the invention is a chimeric antibody. By the expression "chimeric antibody" is meant an antibody that is composed of variables regions from a murine immunoglobulin and of constant regions of a human immunoglobulin. This alteration consists simply of substituting the mouse constant region by a human constant region, thus resulting in a humnan/murine chimera which may have sufficiently low immunogenicity to be acceptable for pharmaceutical use. For the present invention, said chimeric antibody comprises the constant regions from human light and heavy chains. A number of methods for producing such chimeric antibodies have yet been reported, thus forming part of the general knowledge of the skilled artisan (See, e.g., U.S. Pat. No. 5,225,539).

According to another preferred embodiment, the antibody of the invention is a humanized antibody.

By "humanized antibody" is meant an antibody that is composed partially or fully of amino acid sequences derived from a human antibody germline by altering the sequence of an antibody having non-human complementarity determining regions (CDR). This humanization of the variable region of the antibody and eventually the CDR is made by techniques that are by now well known in the art.

As an example, British Patent Application GB 2188638A and U.S. Pat. No. 5,585,089 disclose processes wherein recombinant antibodies are produced where the only portion of the antibody that is substituted is the complementarity determining region, or "CDR.". The CDR grafting technique has been used to generate antibodies which consist of murine CDRs, and human variable region framework and constant regions (See. e.g., RIECHMANN et al., *Nature*, vol. 332, p: 323-327, 1988). These antibodies retain the human constant regions that are necessary for Fc dependent effector function, but are much less likely to evoke an immune response against the antibody.

As an example, the framework regions of the variable regions are substituted by the corresponding human framework regions leaving the non-human CDR substantially intact, or even replacing the CDR with sequences derived from a human genome. Fully human antibodies are produced in genetically modified mice whose immune systems have been altered to correspond to human immune systems. As mentioned above, it is sufficient for use in the methods of the invention, to employ an immunologically specific fragment of the antibody, including fragments representing single chain forms.

A humanized antibody again refers to an antibody comprising a human framework, at least one CDR from a non-human antibody, and in which any constant region present is substantially identical to a human immunoglobulin constant region, i. e., at least about 85 or 90%, preferably at least 95% identical. Hence, all parts of a humanized antibody, except possibly the CDRs, are substantially identical to corresponding parts of one or more native human immunoglobulin sequences. For example, a humanized immunoglobulin would typically not encompass a chimeric mouse variable region/human constant region antibody.

Humanized or chimeric antibodies have at least three potential advantages over non-human antibodies for use in human therapy:

1) Because the effector portion is human, it may interact better with the other parts of the human immune system (e.g., destroy the target cells more efficiently by complement-dependent cytotoxicity (CDC) or antibody-dependent cellular cytotoxicity (ADCC)).

2) The human immune system should not recognize the framework or C region of the humanized antibody as foreign, and therefore the antibody response against such an injected antibody should be less than against a totally foreign non-human antibody or a partially foreign chimeric antibody.

3) Injected non-human antibodies have been reported to have a half-life in the human circulation much shorter than the half-life of human antibodies, Injected humanized antibodies will have a half-life essentially identical to naturally occurring human antibodies, allowing smaller and less frequent doses to be given.

As an example, the design of humanized immunoglobulins may be carried out as follows: When an amino acid falls under the following category, the framework amino acid of a human immunoglobulin to be used (acceptor immunoglobulin) is replaced by a framework amino acid from a CDR-providing non-human immunoglobulin (donor immunoglobulin): (a) the amino acid in the human framework region of the acceptor immunoglobulin is unusual for human immunoglobulin at that position, whereas the corresponding amino acid in the donor immunoglobulin is typical for human immunoglobulin at that position; (b) the position of the amino acid is immediately adjacent to one of the CDRs; or (c) any side chain atom of a framework amino acid is within about 5-6 angstroms (center-to-center) of any atom of a CDR amino acid in a three dimensional immunoglobulin model (QUEEN et al., *Proc. Natl. Acad. Sci. USA*, vol. 88, p:2869, 1991). When each of the amino acid in the human framework region of the acceptor immunoglobulin and a corresponding amino acid in the donor immunoglobulin is unusual for human immunoglobulin at that position, such an amino acid is replaced by an amino acid typical for human immunoglobulin at that position.

Advantageously, said antibody comprises the light chain variable region (LCVR) with the amino acid sequence SEQ id no: 6 and/or the heavy chain variable region (HCVR) with the amino acid sequence SEQ id no: 7.

| SEQ id no: 6 | DVVMTQTPLS | LPVSLGDQAS | ISCRSSQSLL | KNNGNTFLHW |
|---|---|---|---|---|
| | YLQKSGQSPK | LLIYKVSNRL | SGVPDRFSGS | GSGTYFTLKI |
| | SRVEAEDLGV | YFCSQSTHIP | YTFGGGTKLE | IK |

| SEQ ID no: 7 | EVKLVESGGG | LVLPGDSLRL | SCATSEFTFT | DYYMTWVRQP |
|---|---|---|---|---|
| | PRKALEWLGF | IRNRANGYTT | EYNPSVKGRF | TISRDNSQSI |
| | LYLQMNTLRT | FDSATYYCAR | VSNWAFDYWG | QGTTLTVSS |

A human kappa (κ) CL domain is well known from the skilled person and corresponds, as an example, to SEQ id no 8.

| SEQ id no: 8 | RTVAAPSVFIFPPSDEQLKSGTASVVCLLNNFYPREAKVQWKV |
|---|---|
| | DNALQSGNSQESVTEQDSKDSTYSLSSTLTLSKADYEKHKVYA |
| | CEVTHQGLSSPVTKSFNRGEC |

Preferably, the antibody of the invention has a light chain having the amino acid sequence SEQ id no 9.

| SEQ id no: 9 | DVVMTQTPLSLPVSLGDQASISCRSSQSLLKNNGNTFLHWYLQ |
|---|---|
| | KSGQSPKLLIYKVSNRLSGVPDRFSGSGSGTYFTLKISRVEAE |
| | DLGVYFCSQSTHIPYTGGGTKLEIKRTVAAPSVFIFPPSDEQL |
| | KSGTASVVCLLNNFYPREAKVQWKVDNALQSGNSQESVTEQDS |
| | KDSTYSLSSTLTLSKADYEKHKVYACEVTHQGLSSPVTKSFNR |
| | GEC |

CH2 and CH3 domains from a human IgG1 are well known from the skilled person and correspond as an example to SEQ id no 10.

| SEQ id no: 10 | APELLGGPSVFLFPPKPKDTLMISRTPEVTCVVVDVSHEDPEV |
|---|---|
| | KFNWYVDGVEVHNAKTKPREEQYNSTYRVVSVLTVLHQDWLNG |
| | KEYKCKVSNKALPAPIEKTISKAKGQPREPQVYTLPPSREEMT |
| | KNQVSLTCLVKGFYPSDIAVEWESNGQPENNYKTTPPVLDSDG |
| | SFFLYSKLTVDKSRWQQGNVFSCSVMHEALHNHYTQKSLSLSP |
| | GK |

CH1 domain from a human IgG1 is well known from the skilled person. As used herein, a "CH1 domain, which is mutated so as to restore the pairing between the CH1 and light chain typical of the other IgG subclasses", refers to a human CH1 domain from a human IgG1 wherein an amino acid has been substituted by a cysteine residue, preferably so as to present a cysteine residue at the 133 or 134 position of the CH1 sequence. The numbering of the constant region is that of the EU index as set forth in Kabat et al. (1991, NIH Publication no 91-3242, National technical Information Service Springfield, Va.). As an example, the CH1 domain from a human IgG1 corresponds to SEQ id no:29. Said CH1 domain, when mutated so as to restore the typical IgG pairing between CH1 and light chains typical of the other IgG subclasses corresponds to the amino acid sequence SEQ id no 11, wherein the serine residue in position 133 has been substituted by a cysteine or to the amino acid sequence SEQ id no:30, wherein the serine residue in position 134 has been substituted by a cysteine. The cysteine residue at the 133 or 134 position of the CH1 sequence restores a disulfide bound between the light chain and the heavy chain of the antibodies of the invention.

| | |
|---|---|
| SEQ id no: 29 | ASTKGPSVFPLAPSSKSTSGGTAALGUNKDYFPEPVTVSWN SGALTSGVHTFPAVLQSSGLYSLSSVVTVPSSSLGTQTYIC̲N̲ VNHKPSNTKVDKKV |
| SEQ id no: 11 | ASTKGPSVFPLAPCSKSTSGGTAALGCLVKDYFPEPVPISW NSGALTSGVHTFPAVLQSSGLYSLSSVVTVPSSSLGTQTYIC̲ NVNHKPSNTKVDKKV |
| SEQ id no: 30 | ASTKGPSVFPLAPSCKSTSGGTAALGCLVKDYFPEPVTVSW NSGALTSGVHTFPAVLQSSGLYSLSSVVTVPSSSLGTQTYIC̲ NVNHKPSNTKVDKKV |

CH1 domain from a human IgG2, IgG3, and IgG4 are well known from the skilled person. As an example, CH1 domain from a human IgG2 corresponds to SEQ id no 31, the CH1 domain from a human IgG3 corresponds to SEQ id no 12, and the CH1 domain from a human IgG4 corresponds to SEQ id no 32.

| | |
|---|---|
| SEQ id no: 31 | ASTKGPSVFPLAPCSRSTSESTAALGCLVKDYFPEPVTVSWN SGALTSGVHTFPAVLQSSGLYSLSSVVTVPSSNFGTQTYTCN VDHKPSNTKVDKTV |
| SEQ id no: 12 | ASTKGPSVFPLAPCSRSTSGGTAALGCLVKDYFPEPVTVSW NSGALTSGVHTFPAVLQSSGLYSLSSVVTVPSSSLGTQTYTC NVNHKPSNTKVDKRV |
| SEQ id no: 32 | ASTKGPSVFPLAPCSRSTSESTAALGCLVKDYFPEPVTVSWN SGALTSGVHTFPAVLQSSGLYSLSSVVTVPSSSLGTKTYTCN VDHKPSNTKVDKRV |

According to a first preferred embodiment, the antibody of the invention comprises a mutated CH1 domain from a human IgG1 presenting a cysteine residue at the 133 or 134 position of its sequence, preferably said domain has the sequence SEQ id no 11.

Still preferably, said antibody is selected in the group comprising 301.14a, 301.14b, 301.16 and 301.18.

According to a second preferred embodiment, the chimeric antibody of the invention comprises a CH1 domain from a human IgG2, IgG3 or IgG4, preferably said domain is a CH1 domain from an IgG3, such as the sequence SEQ id no 12.

Still preferably, said antibody is selected in the group comprising 301.15, 301.15b, 301.17 and 301.19.

The chimeric antibody of the invention also comprises a hinge domain from a human IgG1, IgG2, IgG3, IgG4 or a derivative thereof.

The hinge domain from a human IgG1 is well known from the skilled person and corresponds as an example to SEQ id no 13. Derivative of hinge domain from a human IgG1 corresponds typically to a hinge domain, wherein the cysteine residue at the fifth position of the hinge sequence has been substituted by another residue, in fact, said mutation results in the restoration of the structure typical of the other IgG subclasses. As an example of such derivative, one can cite SEQ id no 14.

| | |
|---|---|
| SEQ id no: 13 | EPKSCDKTHTCPPCP |
| SEQ id no: 14 | EPKSSDKTHTCPPCP |

Hinge domain from a human IgG2, IgG3 or IgG4 are well known from the skilled person and corresponds as an example to SEQ id no 15 for IgG3. Derivatives of human IgG3 are also well known from the skilled person and correspond as an example to SEQ id no 16 to 19, preferably SEQ id no 19.

| | |
|---|---|
| SEQ id no: 15 | ELKTPLGDTTHTCPRCPEPKSCDTPPPCPRCPEPKS CDTPPPCPRCPEPKSCDTPPPCPRCP |
| SEQ id no: 16 | ELKTPLGDTTHTCPRCPEPKSCDTPPPCPRCPEPKS CDTPPPCPRCP |
| SEQ id no: 17 | ELKTPLGDTTHTCPRCPEPKSCDTPPPCPRCP |
| SEQ id no: 18 | EPKSCDTPPPCPRCP |
| SEQ id no: 19 | ELKTPLGDTTHTCPRCP |

According to a third preferred embodiment, the antibody of the invention comprises a hinge domain from a human IgG1 or a derivative thereof, preferably said domain has the sequence SEQ id no 13 or SEQ id no 14.

Still preferably, said antibody is selected in the group comprising 301.14a, 301.14b, 301.15, 301.15b, 301.20 and 301.21.

According to a forth preferred embodiment, the antibody of the invention comprises a hinge domain from a human IgG2, IgG3, IgG4 or a derivative thereof, preferably said domain is from a human IgG3 and has the sequence selected in the group consisting of SEQ id no 15 to SEQ id no 19, and most preferably SEQ id no 15 or SEQ id no 19.

Still preferably, said antibody is selected in the group comprising 301.16, 301.17, 301.18 and 301.19.

According to a fifth preferred embodiment, the antibody of the invention comprises:
1) a light chain having the amino acid sequence SEQ id no 9,
2) a heavy chain consisting of:
   the CH2 and CH3 domains from a human IgG1 having the sequence SEQ id no 10,
   an amino acid sequence corresponding to human CH1 and hinge domains selected in the group comprising or consisting of:

| Sequence | Antibody | FIG. |
|---|---|---|
| SEQ id no: 20 | 301.14a | 2 |
| SEQ id no: 21 | 301.14b | 3 |
| SEQ id no: 22 | 301.15 | 4 |
| SEQ id no: 34 | 301.15b | 9 |
| SEQ id no: 23 | 301.16 | 5 |
| SEQ id no: 24 | 301.17 | 6 |
| SEQ id no: 25 | 301.18 | 7 |
| SEQ id no: 26 | 301.19 | 8 |

-continued

| Sequence | Antibody | FIG. |
|---|---|---|
| SEQ id no: 31 | 301.20 | 10 |
| SEQ id no: 32 | 301.21 | 11 |

According to a still preferred embodiment, the antibody of the invention is selected among the 301.15, 301.18 and 301.19 antibodies.

In fact, these antibodies show unexpectedly a pro-apoptotic activity greater than the one of the original antibody.

Still preferably, the antibody of the invention is the 301.15 antibody.

In fact, this antibody is the only one showing a binding cooperativity as for the original antibody.

Preferably, the introduction of a cysteine residue within the antibodies of the invention either by a mutated CH1 domain from a human IgG1 presenting a cysteine residue at the 133 or 134 position of its sequence, or by a CH1 domain from a human IgG2, IgG3 or IgG4 do not liberate any free thiol group previously linked to another cysteine residue.

The antibodies of the invention encompass immunoconjugates.

As used herein, the term "immunoconjugate" refers to a conjugate molecule comprising at least one chimeric antibody or a functional fragment thereof, bound to a second molecule, preferably a cytotoxic agent or a radioisotope. Preferably, said antibody or functional fragment thereof is bound to said second molecule by covalent linkage.

In one embodiment, the antibody of the invention is an immunoconjugate.

In a particular embodiment, the antibody of the invention is an immunoconjugate wherein said immunoconjugate comprises a antibody of the invention or a functional fragment thereof and a cytotoxic agent.

In another particular embodiment, the antibody of the invention is an immunoconjugate wherein said immunoconjugate comprises a antibody of the invention or a functional fragment thereof and a radioisotope.

According to a second aspect, the present invention is related to a pharmaceutical composition comprising at least one antibody as described herein, or at least one functional fragment thereof and a pharmaceutically acceptable carrier for use in therapy.

Said composition is particularly useful for treating cancer expressing the GD2-O-acetylated ganglioside.

Said composition may be in any pharmaceutical form suitable for administration to a patient, including but not limited to solutions, suspensions, lyophilized powders, capsule and tablets.

The pharmaceutical compositions of the invention may further comprise any pharmaceutically acceptable diluent, excipient or auxiliary.

The pharmaceutical composition of the invention may be formulated for injection, e.g. local injection, transmucosal administration, inhalation, oral administration and more generally any formulation that the skilled person finds appropriate to achieve the desired therapy.

The antibody of the invention is contained in said pharmaceutical composition in an amount effective to achieve the intended purpose, and in dosages suitable for the chosen route of administration.

More specifically, a therapeutically effective dose means an amount of a compound effective to prevent, alleviate or ameliorate symptoms of the subject suffering from cancer.

Depending on the intended application, the chimeric antibody of the invention may further comprise additional constituents. As an example, the chimeric antibody of the invention may correspond to an immunoconjugate.

A third aspect of the present invention concerns a method for treating cancer expressing the GD2-O-acetylated ganglioside comprising providing to a patient in need thereof a pharmaceutical composition as described herein, which comprises at least one chimeric antibody as described herein, or at least one functional fragment thereof.

As used herein, the term "patient" refers to a mammal, preferably to a human.

Preferably, a patient in need thereof corresponds to a patient suffering from a cancer expressing the GD2-O-acetylated ganglioside.

Said cancer expressing the GD2-O-acetylated ganglioside are selected in the group comprising neuroblastomas, melanomas, glioblastomas, small cell lung cancers, breast cancers and cancer stem cell cancers.

A fourth aspect of the present invention concerns a method for increasing the therapeutic efficacy of human IgG1 antibody which binds specifically to the O-acetylated-GD2 ganglioside, derivative or a functional fragment thereof, comprising the step of mutating the human CH1γ1 domain from said antibody, so as to restore the pairing between CH1 and CL domains that is typical of other IgG subclasses, or by substituting said human CH1γ1 domain by the CH1 domain from a human IgG2 (CH1γ2), IgG3 (CH1γ3) or IgG4 (CH1γ4).

Said method of increasing the therapeutic efficacy comprises increasing the pro-apoptotic activity of said antibody.

In a first preferred embodiment, the method of the invention comprises the step of mutating the CH1 domain from a human IgG1 antibody which binds specifically to the O-acetylated-GD2 ganglioside, so as to restore the pairing between CH1 and CL domains that is typical of other IgG subclasses.

CH1 domain from a human IgG1 is well known from the skilled person.

CH1 domain from a human IgG1 antibody which binds specifically to the O-acetylated-GD2 ganglioside can be shown on FIG. 1.

Advantageously, the step of mutating the CH1 domain of a human IgG1 antibody which binds specifically to the O-acetylated-GD2 ganglioside, so as to restore the pairing between CH1 and CL domains that is typical of other IgG subclasses, is done by:

a) isolating a nucleic acid sequence comprising the CH1 domain of a human IgG1 antibody which binds specifically to the O-acetylated-GD2 ganglioside, said nucleic acid sequence preferably encoding the heavy chain of the antibody;

b) mutating a codon, preferably mutating the codon encoding position 133 or 134 of said CH1 domain to encode the amino acid residue cysteine (C) to provide a mutated nucleic acid sequence;

c) providing the mutated nucleic acid sequence with operable expression elements;

d) co-expressing the mutated nucleic acid with a nucleic acid sequence encoding the light chain of the antibody in a suitable host thereby providing a mutated human IgG1 antibody which binds specifically to the O-acetylated-GD2 ganglioside, derivative or a functional fragment; and e) optionally, isolating the mutated antibody, derivative or fragment thereof.

In a second preferred embodiment, the method of the invention comprises the step of substituting said CH1 domain from a human IgG1 by the CH1 domain from a human IgG2, IgG3 or IgG4.

CH1 domain from a human IgG2, IgG3 and IgG4 are well known from the skilled person. As an example, the CH1 domain from a human IgG3 corresponds to SEQ id no 12.

Advantageously, the step of substituting the CH1 domain of a human IgG antibody which binds specifically to the O-acetylated-GD2 ganglioside by the CH1 domain from a human IgG2, IgG3 or IgG4 is done by:

a) isolating a nucleic acid sequence comprising the CH1 domain of a human IgG1 antibody which binds specifically to the O-acetylated-GD2 ganglioside, said nucleic acid sequence preferably encoding the heavy chain of the antibody;

b) substituting said CH1 domain of a human IgG1 antibody which binds specifically to the O-acetylated-GD2 ganglioside nucleic acid by a nucleic acid sequence encoding the CH1 domain from a human IgG2, IgG3 or IgG4 to provide a mutated nucleic acid sequence;

c) providing the mutated nucleic acid sequence with operable expression elements;

d) co-expressing the mutated nucleic acid with a nucleic acid sequence encoding the light chain of the antibody in a suitable host thereby providing a mutated human IgG1 antibody which binds specifically to the O-acetylated-GD2 ganglioside, derivative or a functional fragment; and e) optionally, isolating the mutated antibody, derivative or fragment thereof.

In a still preferred embodiment, the method of the invention further comprises the step of mutating the hinge IgG1 domain from a human IgG1 antibody which binds specifically to the O-acetylated-GD2 ganglioside, so as to restore the pairing between the hinge and CH2 domain that is typical of other IgG subclasses, or of substituting human hinge IgG1 domain of said antibody by the hinge domain from a human IgG2, IgG3 or IgG4, or a derivative thereof.

The hinge domain from a human IgG1 is well known from the skilled person and corresponds as an example to SEQ id no 13.

As used herein, the step of "mutating the hinge domain from a human IgG1 antibody which binds specifically to the O-acetylated-GD2 ganglioside, so as to restore the pairing between hinge and CH2 domains that is typical of other IgG subclasses", refers to a human IgG1 hinge domain of said antibody, wherein the cysteine residue at the fifth position of the hinge proteic sequence has been substituted by another residue, preferably by a serine. In fact, said mutation results in the restoration of the typical IgG structure. As an example of such derivative, one can cite SEQ id no 14.

Advantageously, the step of mutating the human hinge from said antibody, so as to restore the pairing between hinge and the CH12 that is typical of other IgG subclasses is done by:

a) isolating a nucleic acid sequence comprising the hinge domain of a human IgG1 antibody which binds specifically to the O-acetylated-GD2 ganglioside, said nucleic acid sequence preferably encoding the heavy chain of the antibody;

b) mutating the codon encoding the amino acid residue cysteine (C) at position 5 of said hinge domain to encode another amino acid residue, preferably a serine residue, to provide a mutated nucleic acid sequence;

c) providing the mutated nucleic acid sequence with operable expression elements;

d) co-expressing the mutated nucleic acid with a nucleic acid sequence encoding the light chain of the antibody in a suitable host thereby providing a mutated human IgG1 antibody which binds specifically to the O-acetylated-GD2 ganglioside, derivative or a functional fragment; and e) optionally, isolating the mutated antibody, derivative or fragment thereof.

Hinge domain from a human IgG2, IgG3 or IgG4 are well known from the skilled person and corresponds as an example to SEQ id no 15 for IgG3. Derivatives of human IgG3 are also well known from the skilled person and correspond as an example to SEQ id no 16 to 19, preferably SEQ id no 19.

Still advantageously, the step of substituting human hinge IgG1 domain of said antibody by the hinge domain from a human IgG2, IgG3 or IgG4, or a derivative thereof, is done by:

a) isolating a nucleic acid sequence comprising the hinge domain of a human IgG1 antibody which binds specifically to the O-acetylated-GD2 ganglioside, said nucleic acid sequence preferably encoding the heavy chain of the antibody;

b) substituting the hinge domain of a human IgG1 antibody which binds specifically to the O-acetylated-GD2 ganglioside nucleic acid sequence by a nucleic acid sequence encoding the hinge domain from a human IgG2, IgG3, IgG4 or a derivative to provide a mutated nucleic acid sequence;

c) providing the mutated nucleic acid sequence with operable expression elements;

d) co-expressing the mutated nucleic acid with a nucleic acid sequence encoding the light chain of the antibody in a suitable host thereby providing a mutated human IgG1 antibody which binds specifically to the O-acetylated-GD2 ganglioside, derivative or a functional fragment; and e) optionally, isolating the mutated antibody, derivative or fragment thereof.

Other embodiments and advantages of the present invention are illustrated in the following non-limiting examples.

EXAMPLES

1—Pro-Apoptotic Activity of Anti-OAcGD2 Antibody In Vitro

In a first step, the chimeric anti-OAcGD2 antibody, c8B6, has been designed from 8B6 by substituting its constant regions by the one of a human IgG1,κ. Its sequences are represented in FIG. 1 (SEQ id no 27 and SEQ id no 28).

The structure of this antibody comprises 2 intramolecular disulfide bonds in light chain (Cys23-Cys93 and Cys139-Cys199), and 4 intramolecular disulfide bonds in heavy chain (Cys22-Cys98, Cys146-Cys202, Cys263-Cys323, and Cys369-Cys427. Cysteine residues involved in intra-chain disulfide bonds are indicated by a star (*). The whole structure is stabilized by 3 intermolecular disulfide bonds: light chain is connected to heavy chain by one disulfide bond between the last cysteine residue of light chain and the cysteine residue of the upper hinge region (Cys219-Cys222), and heavy chains are connected by 2 disulfide bonds connecting the Cysteine in the middle hinge (Cys228-Cys228 and Cys231-Cys231). Cysteine residues involved in inter-chain disulfide bonds are indicated by a arrow (↑).

The 8B6 LCVR is cloned NotI-KasI in a pEvi vector so as to be fused with the CL domain of a human IgG1.

The 8B6 HCVR domain is cloned NotI-NheI in a pEvi' vector so as to be fused with the constant domain of the heavy chain of a human IgG1.

Then, CHO K1 cells are co-transfected by both vectors.

After transfection, the CHO K1 cells are maintained in a serum free medium for several days.

Each day, the culture medium is harvested and freezed at −80° C. A new medium is added to the transfected cells until the cell viability is less than 70-80%.

The harvested culture media are pooled and the antibody is purified using protein A immobilized on a sepharose matrix.

The production of c8B6 in CHO was analyzed by electrophoresis under both reducing and non-reducing conditions. The results have shown that under non-reducing conditions, the c8B6 antibody showed one band at 150 kD corresponding to whole antibody. While, under reducing conditions, a band at 50 kD for HC and a band at 25 kD for LC were observed. The gel filtration on a SUPERDEX Column showed a chromatogram profile with a main peak (99.0% for the degree purity) at 12.3 ml corresponding to 150 kD. Finally, the yield of production for the chimeric c8B6 after purification on a protein A* column was about 315 mg/L of supernatant.

The binding of the antibody to its target was confirmed by flow cytometry on IMR5 cells expressing GD2-O-Acetylated ganglioside. The binding was revealed by a goat anti-human IgG conjugated to fluorescein isothiocyanate (FITC). These experiments have confirmed the functionality of this antibody, which binds GD2-O-Acetylated.

Then, the direct cytotoxicity of c8B6 antibody was evaluated by MTT assays.

In these assays, $1\times10^4$ IMR5, SUM159PT or H187 cells are incubated 24 h at 37° C. in a 96-well microplate. Antibodies from 80-0.15 µg/mL were added and incubated 24 h at 37° C. Fifty µg of MTT were then added to each well and incubated at least 4 h at 37° C., before cells were solubilized with 10% SDS and to incubate O.N. at 37° C. The absorbance was then read at 570 and 650 nm. Absorbance of the product at 650 nm was subtracted from the absorbance at 570 nm (Abs570-Abs650) to calculate total conversion of dye. Four control wells with cells treated with 20 µg etoposide provide the blank for absorbance giving the 0% of viability. The inhibition of viability (%) was expressed as a percentage relative to the untreated cells and each value is represented as mean±SEM in quadruplicate.

The results have shown that the antibody c8B6 has lost the direct cytotoxicity of 8B6 following the chimerization step by passing from murine constant IgG3 domains to human IgG1 constant domains. Moreover, the antibody further lost the cooperativity properties of the parental IgG3 8B6.

Finally, many experiments trying different ways of chimerization only restore little pro-apoptotic activity, and no cooperativity in the binding was observed.

Surprisingly, specific modifications of the CH1 constant domain for the chimerization results in great changes for the pro-apoptotic activity.

These results were obtained with the antibodies 301.14a, 301.14b, 301.15, 301.15b, 301.16, 301.17, 301.18, 301.19, 301.20 and 301.21 which were designed on the basis of the previous constructions.

The antibody 301.14a corresponds to a mutated human CH1γ1 (underlined mutation S133C) with the human Hingeγ1 domain as represented in FIG. 2 (SEQ id no 20). The other constant domains correspond to CH2 and CH3 domains of IgG1 (SEQ id no 9) and the kappa CL domain (SEQ id no 8).

The antibody 301.14b corresponds to a mutated human CH1γ1 (underlined mutation S133C) with a mutated human Hingeγ1 domain (underlined mutation corresponding to the substitution of the cysteine 222 by a serine residue, C222S) as represented in FIG. 3 (SEQ id no 21). The other constant domains correspond to CH2 and CH3 domains of IgG1 (SEQ id no 9) and the kappa CL domain (SEQ id no 8).

The antibody 301.15 corresponds to a human CH1γ3 (replacing its cousin CH1γ1) with the human Hingeγ1 domain as represented in FIG. 4 (SEQ id no 22). The other constant domains corresponds to CH2 and CH3 domains of IgG (SEQ id no 9) and the kappa CL domain (SEQ id no 8).

The antibody 301.15b corresponds to a human CH1γ3 (replacing its cousin CH1γ1) with a mutated human Hingeγ1 domain (underlined mutation corresponding to the substitution of the cysteine 222 by a serine residue, C222S) as represented in FIG. 9 (SEQ id no 34). The other constant domains corresponds to CH2 and CH3 domains of IgG1 (SEQ id no 9) and the kappa CL domain (SEQ id no 8).

The antibody 301.16 corresponds to a mutated human CH1γ1 (underlined mutation S133C) with the human Hingeγ3 domain (replacing its cousin Hingeγ1) as represented in FIG. 5 (SEQ id no 23). The other constant domains corresponds to CH2 and CH3 domains of IgG1 (SEQ id no 9) and the kappa CL domain (SEQ id no 8).

The antibody 301.17 corresponds to a human CH1γ3 (replacing its cousin CH1γ1) with the human Hingeγ3 domain (replacing its cousin Hingeγ1) as represented in FIG. 6 (SEQ id no 24). The other constant domains corresponds to CH2 and CH3 domains of IgG1 (SEQ id no 9) and the kappa CL domain (SEQ id no 8).

The antibody 301.18 corresponds to a mutated human CH1γ1 (underlined mutation S133C) with a shortened (17 amino acids) human Hingeγ3 domain as represented in FIG. 7 (SEQ id no 25). The other constant domains corresponds to CH2 and CH3 domains of IgG1 (SEQ id no 9) and the kappa CL domain (SEQ id no 8).

The antibody 301.19 corresponds to a human CH1γ3 (replacing its cousin CH1γ1) with a shortened (17 amino acids) human Hingeγ3 domain as represented in FIG. 8 (SEQ id no 26). The other constant domains corresponds to CH2 and CH3 domains of IgG1 (SEQ id no 9) and the kappa CL domain (SEQ id no 8).

The antibody 301.20 corresponds to a human CH1γ2 (replacing its cousin CH1γ1) with the human Hingeγ1 domain as represented in FIG. 10 (SEQ id no 31). The other constant domains corresponds to CH2 and CH3 domains of IgG1 (SEQ id no 9) and the kappa CL domain (SEQ id no 8).

The antibody 301.21 corresponds to a human CH1γ4 (replacing its cousin CH1γ1) with the human Hingeγ1 domain as represented in FIG. 11 (SEQ id no 32). The other constant domains corresponds to CH2 and CH3 domains of IgG1 (SEQ id no 9) and the kappa CL domain (SEQ id no 8).

The muIgG3 control corresponds to a murine 8B6 IgG3, wherein the CH1 IgG3 corresponds to SEQ id no: 33, wherein the cysteine residue at position 134 is substituted by a serine residue and the serine residue at position 224 is substituted by a cysteine residue.

```
SEQ id no: 33   ATTTAPSVYPLVPGCSDTSGSSVTLGCLVKGYFPEP
                VTVKWNYGALSSGVRTVSSVLQSGFYSLSSLVTVPS
                STWPSQTVICNVAHPASKTELIKRIEPRIPKPCTPP
                GSSCP
```

The binding of said antibodies to GD2-O-Acetylated ganglioside was confirmed as previously.

Then, the potential pro-apoptotic activities of said antibodies were determined as mentioned previously.

The results are summarized in the following tables, wherein the percentage of lysis is the one obtained for antibody concentration of 80 µg/ml.

Direct cytotoxicity of anti-OacGD2 301.14a, 301.14b, 301.15, 301.16, 301.17, 301.18 and 301.19 antibodies on IMR5 cells:

| Construction | Mean +/− SEM of n = 2 experiments | | Affinity (Eq) Kd (nM) |
|---|---|---|---|
| | $EC_{50}$ (µg/ml) | % Maximal lysis | |
| 8B6 | 10.0 ± 1.8 | 33.3 ± 5.6 | 46.9 ± 15.0 |
| c8B6 | 14.7 ± 16.6 | 7.3 ± 5.4 | 208.3 ± 90.9 |
| 301.14a | 6.5 ± 0.3 | 20.2 ± 7.4 | ND |
| 301.14b (n = 1) | 1.0 | 33.8 | 103.6 ± 22.5 |
| 301.15 | 3.6 ± 2.0 | 45.0 ± 13.9 | 161.9 ± 42.0 |
| 301.16 | 2.1 ± 2.0 | 29.2 ± 17.3 | ND |
| 301.17 | 3.2 ± 0.8 | 20.8 ± 3.0 | ND |
| 301.18 | 8.5 ± 0.6 | 31.0 ± 1.7 | 63.9 ± 8.6 |
| 301.19 | 7.6 ± 1.4 | 37.5 ± 0.5 | 54.5 ± 6.2 |

The results show that unexpectedly, the chimeric antibodies comprising a mutated human CH1γ1 or a human CH1γ3 have a pro-apoptotic activity, meaning that loss of direct cytotoxicy might be due to the structure of human IgG1. Moreover, these antibodies all show an $EC_{50}$ greater than the one of the initial antibody 8B6.

The results have also shown that construction that gave the higher cytotoxic effect in terms of maximal % lysis correspond (i) to fusion of human CH1γ3 and human Hingeγ1 (301.15 construct) or (ii) to fusion of human CH1γ1 (mutated on S133C) or human CH1γ3 and shortened-human Hinge γ3 (301.18 and 301.19 constructions). For these 2 latest, an increase of affinity in comparison to original c8B6 was observed.

Finally, and still surprisingly, the 301.15 antibody was the only one to present an aggregative profile in competition curves corresponding to a restored binding cooperativity.

Direct cytotoxicity of anti-OacGD2 301.15b, 301.20 and 301.2 antibodies on IMR5, SUM159PT and H187 cells:

| Cell line | Antibody | % Max lysis (80 µg/ml) | $EC_{50}$ (µg/ml) |
|---|---|---|---|
| IMR5 | 301.15b | 58.67 | 2.53 |
| | 301.20 | 79.92 | 11.60 |
| | 301.21 | 60.88 | 26.12 |
| SUM159PT | 8B6 | 64.76 | 25.42 |
| | 301.14b | 63.99 | 1.92 |
| | 301.15 | 75.53 | 19.19 |
| | c8B6 | 0.00 | ND |
| H187 | 8B6 | 68.46 | 3.30 |
| | 301.14b | 65.42 | 2.27 |
| | 301.15 | 70.96 | 7.72 |
| | c8B6 | 0.00 | ND |

The results show that, unexpectedly, the chimeric antibodies comprising a human CH1γ2 or CH1γ4 have a pro-apoptotic activity on IMR5 cells, meaning that loss of direct cytotoxicy might be due to the structure of human IgG1. Moreover, the chimeric antibodies comprising a human CH1γ3 and a mutated human Hingeγ1 domain (underlined mutation corresponding to the substitution of the cysteine 222 by a serine residue, C222S) have a pro-apoptotic activity on IMR5 cells.

The results have also shown that constructions corresponding to fusion of human CH1γ1 (mutated on S133C) and a mutated human Hingeγ1 domain (underlined mutation corresponding to the substitution of the cysteine 222 by a serine residue, C222S) (301.14b construct) or to fusion of human CH1γ3 and human Hingeγ1 (301.15 construct) have pro-apoptotic activity on both SUM159PT and H187 cells.

Direct cytotoxicity of different antibodies was also assessed by propidium iodine assay.

In this assay, 150000 IMR5 cells were plated in 24-well plates for 24 h at 37° C. and then treated for 24 h at 37° C. with 40 µg/mL of each antibody. Thereafter, dead cells were labeling by propidium iodide (12.5 µg/ml). All samples were analyzed by flow cytometry in a LSRII FACS (Becton Dickinson, San Jose, Calif., USA).

The results are summarized in the following table and illustrated by FIG. 12.

| | % of dead cells | SEM |
|---|---|---|
| PBS | 20.2 | 1.00 |
| c8B6 (301.3) | 22.6 | 1.79 |
| 8B6 (301.4) | 67.7 | 1.90 |
| 301.14b | 46.8 | 2.61 |
| 301.15 | 48.0 | 0.77 |
| huIgG1 control | 20.2 | 0.98 |
| muIgG3 control | 22.4 | 1.59 |

The results confirmed that constructions corresponding to fusion of human CH1 γ1 (mutated on S133C) and a mutated human Hingeγ1 domain (underlined mutation corresponding to the substitution of the cysteine 222 by a serine residue, C222S) (301.14b construct) or to fusion of human CH1γ3 and human Hingeγ1 (301.15 construct) have pro-apoptotic activity on IMR5 cells. Simultaneously, the results confirm that a mutation in the murine IgG3 8B6 so as to mimic the IgG1 structure results in a loss of pro-apoptotic activity.

Reconstituting the pairing between the CH1 and the light chain, typical of non-IgG1 antibodies, could restore pro-apoptotic activity. Such reconstitution could be obtained by restoring the CH1 cysteine typical from non-IgG1 subclasses or by substituting a non-IgG1 CH1 domain.

In conclusion, the inventors succeeded in the chimerization of the 8B6 antibody with a maintained pro-apoptotic activity, which pro-apoptotic activity is even increased for two antibodies, one of which showing also a cooperative binding like the original antibody.

2—Anti-OAcGD2 Antibody Efficiency In Vivo

Murine Neuroblastoma Model

NOD/SCID mice, aged 5 weeks, were purchased from CHARLES RIVER.

The human neuroblastoma IMR5 tumors were grown in immunodeficient NOD-SCID mice. Briefly, mice were injected subcutaneously with tumor cells ($1 \times 10^6$ IMR5 cells) on the right flank. Subcutaneous tumor growth was then measured after tumor implantation using the formula [Volume $mm^3$=(length)×(width$^2$)×0.5]. In the IMR5 human neuroblastoma-bearing NOD/SCID mice, antibody (500µ/mouse) was given i.v. when the tumor volume was equal to 0.1 $cm^3$.

Mice received 8B6 (muIgG3) mAb, or c.8B6 (huIgG1) mAb, or double mutated huIgG1 mAb, or huIgG1 CH1 substituted by huIgG3 CH1.

The invention claimed is:

1. An antibody, or functional fragment thereof, which binds specifically to the 0-acetylated-GD2 ganglioside, said antibody comprising:
   a) a light chain comprising three light chain complementary regions (CDRs) having the following amino acid sequences:
      i) the light chain CDR1: QSLLKNNGNTFL (SEQ id no 1);
      ii) the light chain CDR2: KVS;
      iii) the light chain CDR3: SQSTHIPYT (SEQ id no 2); and
      a light chain framework sequence of an immunoglobulin light chain, wherein said framework sequence comprises a human kappa (κ) CL domain; and
   b) a heavy chain comprising three heavy chain complementary regions (CDRs) having the following amino acid sequences:
      i) the heavy chain CDR1: EFTFTDYY (SEQ id no 3);
      ii) the heavy chain CDR2: IRNRANGYTT (SEQ id no 4);
      iii) the heavy chain CDR3: ARVSNWAFDY (SEQ id no 5); and
      a heavy chain framework sequence of an immunoglobulin heavy chain, wherein said framework sequence comprises:
      1) the CH2 and CH3 domains of a human IgG1, and
      2) a mutated CH1 domain of a human IgG1, wherein the amino acid residue at position 133 or 134 is substituted by a cysteine residue, so as to restore the pairing between CH1 and CL domains that is typical of human IgG2, IgG3 and igG4 subclasses, or a CH1 domain of a human IgG2, IgG3 or IgG4, wherein the antibody has an increased pro-apoptotic activity as compared to the same antibody having native CH1γ1 domain, of the same binding specificity under the same conditions, and
   wherein the cysteine residue introduced within the CH1 domain do not liberate any free thiol group previously bonded to another cysteine residue anywhere in the antibody molecule.

2. The antibody of claim 1, wherein said antibody or functional fragment thereof, which binds specifically to the O-acetylated-GD2 ganglioside presents a $K_D$ of less than $2 \times 10^{-7}$ M for said ganglioside.

3. The antibody of claim 1, wherein said antibody comprises the light chain variable region (LCVR) having the amino acid sequence SEQ id no 6, and/or the heavy chain variable region (HCVR) with the amino acid sequence SEQ id no 7.

4. The antibody of claim 1, wherein said antibody comprises a human kappa (κ) CL domain having the sequence SEQ id no 8.

5. The antibody of claim 4, wherein said antibody has a light chain having the amino acid sequence SEQ id no 9.

6. The antibody of claim 1, wherein said antibody comprises the CH2 and CH3 domains of a human IgG1 having the sequence SEQ id no 10.

7. The antibody of claim 1, wherein said antibody comprising the mutated CH1 domain of a human IgG1 so as to restore the pairing between CH1 and CL domains that is typical of human IgG2, IgG3 and IgG4 subclasses, comprises the amino acid sequence of SEQ id no 11 or of SEQ id no 30.

8. The antibody of claim 1, wherein said antibody comprises a CH1 domain of a human IgG3 having the amino acid sequence of SEQ id no 12.

9. The antibody of claim 1, wherein said antibody also comprises a hinge domain of a human IgG1, IgG2, IgG3, IgG4 or a derivative of hinge domain of a human IgG1 or IgG3.

10. The antibody of claim 9, wherein said hinge domain is selected in the group comprising SEQ id no 13 to SEQ id no 19.

11. The antibody of claim 1, wherein said antibody comprises:
   1) a light chain having the amino acid sequence SEQ id no 9, and
   2) a heavy chain consisting of:
      the CH2 and CH3 domains of a human IgG1 having the sequence SEQ id no 10, and
      an amino acid sequence corresponding to human CH1 and hinge domains selected in the group comprising or consisting of:

| Sequence | antibody | FIG. |
| --- | --- | --- |
| SEQ id no: 20 | 301.14a | 2 |
| SEQ id no: 21 | 301.14b | 3 |
| SEQ id no: 22 | 301.15 | 4 |
| SEQ id no: 34 | 301.15b | 9 |
| SEQ id no: 23 | 301.16 | 5 |
| SEQ id no: 24 | 301.17 | 6 |
| SEQ id no: 25 | 301.18 | 7 |
| SEQ id no: 26 | 301.19 | 8 |
| SEQ id no: 31 | 301.20 | 10 |
| SEQ id no: 32 | 301.21 | 11. |

12. The antibody of claim 11, wherein said antibody is 301.14b, 301.15, 301.18 or 301.19, preferably 301.15.

13. The antibody of claim 1, wherein said antibody is an immunoconjugate.

14. A pharmaceutical composition comprising at least one antibody according to claim 1, and a pharmaceutically acceptable carrier.

15. The pharmaceutical composition of claim 14, wherein said composition is for treating cancer expressing the GD2-O-acetylated ganglioside such as neuroblastomas, melanomas, glioblastomas, small cell lung cancers, breast cancers and cancer stem cell cancers.

16. A method for increasing the pro-apoptotic activity of an antibody which binds specifically to the O-acetylated-GD2 ganglioside, or a functional fragment thereof,
   wherein said antibody comprises:
   a) a light chain comprising three light chain complementary regions (CDRs) having the following amino acid sequences:
      i) the light chain CDR1: QSLLKNNGNTFL (SEQ id no 1);
      ii) the light chain CDR2: KVS;
      iii) the light chain CDR3: SQSTHIPYT (SEQ id no 2); and
      a light chain framework sequence of an immunoglobulin light chain, wherein said framework sequence comprises a human kappa (κ) CL domain; and
   b) a heavy chain comprising three heavy chain complementary regions (CDRs) having the following amino acid sequences:
      i) the heavy chain CDR1: EFTFTDYY (SEQ id no 3);
      ii) the heavy chain CDR2: IRNRANGYTT (SEQ id no 4);
      iii) the heavy chain CDR3: ARVSNWAFDY (SEQ id no 5); and a heavy chain framework sequence of an immunoglobulin heavy chain, wherein said framework sequence comprises:
  1) the CH2 and CH3 domains of a human IgG1, and
  2) the CH1 domain of a human IgG1,
said method comprising the step of mutating the human CH1γ1 domain of said antibody by substituting the amino acid residue at position 133 or 134 by a cysteine, so as to restore the pairing between CH1 and CL domains that is typical of human IgG2, IgG3 and IgG4 subclasses, or by substituting said human CH1γ1 domain by the CH1 domain of a human IgG2 (CH1γ2), IgG3 (CH1γ3) or IgG4 (CH1γ4), wherein the mutating or substituting of CH1γ1 results in an increased therapeutic efficacy of the antibody as compared to the same antibody having native CH1γ1 domain of the same binding specificity under the same conditions, wherein the cysteine residue introduced within the CH1 domain do not liberate any free thiol group previously bonded to another cysteine residue anywhere in the antibody molecule.

17. The method according to claim 16, wherein the step of mutating the human CH1γ1 domain of said antibody, so as to restore the pairing between CH1 and CL domains that is typical of human IgG2, IgG3 and IgG4 subclasses, is done by:
  a) isolating a nucleic acid sequence comprising the CH1 domain of a human IgG1 antibody which binds specifically to the O-acetylated-GD2 ganglioside, said nucleic acid sequence preferably encoding the heavy chain of the antibody;
  b) mutating a codon encoding position 133 or 134 of said CH1 domain to encode the amino acid residue cysteine (C) to provide a mutated nucleic acid sequence;
  c) providing the mutated nucleic acid sequence with operable expression elements;
  d) co-expressing the mutated nucleic acid with a nucleic acid sequence encoding the light chain of the antibody in a suitable host thereby providing a mutated human IgG1 antibody which binds specifically to the O-acetylated-GD2 ganglioside, or a functional fragment; and
  e) optionally, isolating the mutated antibody, or fragment thereof.

18. The method according to claim 16, wherein the step of substituting the CH1γ1 domain of said antibody by the CH1 domain of a human IgG2, IgG3 or IgG4 is done by:
  a) isolating a nucleic acid sequence comprising the CH1 domain of a human IgG1 antibody which binds specifically to the O-acetylated-GD2 ganglioside, said nucleic acid sequence preferably encoding the heavy chain of the antibody;
  b) substituting said CH1 domain of a human IgG1 antibody which binds specifically to the O-acetylated-GD2 ganglioside nucleic acid by a nucleic acid sequence encoding the CH1 domain of a human IgG2, IgG3 or IgG4 to provide a mutated nucleic acid sequence;
  c) providing the mutated nucleic acid sequence with operable expression elements;
  d) co-expressing the mutated nucleic acid with a nucleic acid sequence encoding the light chain of the antibody in a suitable host thereby providing a mutated human IgG1 antibody which binds specifically to the O-acetylated-GD2 ganglioside, or a functional fragment; and
  e) optionally, isolating the mutated antibody, or fragment thereof.

19. The method according to claim 16, said method further comprises the step of mutating the hinge IgG1 domain of a human IgG1 antibody which binds specifically to the O-acetylated-GD2 ganglioside, so as to restore the pairing between the hinge and CH2 domain that is typical of human IgG2, IgG3 and IgG4 subclasses, or of substituting human hinge IgG1 domain of said antibody by the hinge domain of a human IgG2, IgG3 or IgG4, or a derivative hinge domain of human IgG3.

20. The method according to claim 19, wherein the step of mutating the human hinge of said antibody, so as to restore the pairing between hinge and the CH2 that is typical of human IgG2, IgG3 and IgG4 subclasses is done by:
  a) isolating a nucleic acid sequence comprising the hinge domain of a human IgG1 antibody which binds specifically to the O-acetylated-GD2 ganglioside, said nucleic acid sequence preferably encoding the heavy chain of the antibody;
  b) mutating the codon encoding the amino acid residue cysteine (C) at position 5 of said hinge domain to encode another amino acid residue, preferably a serine residue, to provide a mutated nucleic acid sequence;
  c) providing the mutated nucleic acid sequence with operable expression elements;
  d) co-expressing the mutated nucleic acid with a nucleic acid sequence encoding the light chain of the antibody in a suitable host thereby providing a mutated human IgG1 antibody which binds specifically to the O-acetylated-GD2 ganglioside, or a functional fragment; and
  e) optionally, isolating the mutated antibody, or fragment thereof.

21. The method according to claim 19, wherein the step of substituting human hinge IgG1 domain of said antibody by the hinge domain of a human IgG2, IgG3 or IgG4, or a derivative of hinge domain of human IgG3, is done by:
  a) isolating a nucleic acid sequence comprising the hinge domain of a human IgG1 antibody which binds specifically to the O-acetylated-GD2 ganglioside, said nucleic acid sequence preferably encoding the heavy chain of the antibody;
  b) substituting the hinge domain of a human IgG1 antibody which binds specifically to the O-acetylated-GD2 ganglioside nucleic acid sequence by a nucleic acid sequence encoding the hinge domain of a human IgG2, IgG3, IgG4 or a derivative of hinge domain of human IgG3 to provide a mutated nucleic acid sequence;
  c) providing the mutated nucleic acid sequence with operable expression elements;
  d) co-expressing the mutated nucleic acid with a nucleic acid sequence encoding the light chain of the antibody in a suitable host thereby providing a mutated human IgG1 antibody which binds specifically to the O-acetylated-GD2 ganglioside, or a functional fragment; and
  e) optionally, isolating the mutated antibody, or fragment thereof.

22. The antibody of claim 9, wherein the amino acid residue cysteine (C) at position 5 of the hinge domain of a human IgG1 of SEQ ID NO: 13 is substituted by a serine residue.

23. The antibody of claim 9, wherein the sequence of the derivative of hinge domain of a human IgG3 is selected from the group consisting of SEQ ID NO: 16, SEQ ID NO: 17, SEQ ID NO: 18 and SEQ ID NO: 19.

* * * * *

SEQUENCE LISTING

```
<160> NUMBER OF SEQ ID NOS: 34

<210> SEQ ID NO 1
<211> LENGTH: 12
<212> TYPE: PRT
<213> ORGANISM: Artificial Sequence
<220> FEATURE:
<223> OTHER INFORMATION: CDR1 LC

<400> SEQUENCE: 1

Gln Ser Leu Leu Lys Asn Asn Gly Asn Thr Phe Leu
1               5                   10

<210> SEQ ID NO 2
<211> LENGTH: 9
<212> TYPE: PRT
<213> ORGANISM: Artificial Sequence
<220> FEATURE:
<223> OTHER INFORMATION: CDR3 LC

<400> SEQUENCE: 2

Ser Gln Ser Thr His Ile Pro Tyr Thr
1               5

<210> SEQ ID NO 3
<211> LENGTH: 8
<212> TYPE: PRT
<213> ORGANISM: Artificial Sequence
<220> FEATURE:
<223> OTHER INFORMATION: CDR1 HC

<400> SEQUENCE: 3

Glu Phe Thr Phe Thr Asp Tyr Tyr
1               5

<210> SEQ ID NO 4
<211> LENGTH: 10
<212> TYPE: PRT
<213> ORGANISM: Artificial Sequence
<220> FEATURE:
<223> OTHER INFORMATION: CDR2 HC

<400> SEQUENCE: 4

Ile Arg Asn Arg Ala Asn Gly Tyr Thr Thr
1               5                   10

<210> SEQ ID NO 5
<211> LENGTH: 10
<212> TYPE: PRT
<213> ORGANISM: Artificial Sequence
<220> FEATURE:
<223> OTHER INFORMATION: CDR3 HC

<400> SEQUENCE: 5

Ala Arg Val Ser Asn Trp Ala Phe Asp Tyr
1               5                   10

<210> SEQ ID NO 6
<211> LENGTH: 112
<212> TYPE: PRT
<213> ORGANISM: Artificial Sequence
<220> FEATURE:
<223> OTHER INFORMATION: LCVR
```

-continued

```
<400> SEQUENCE: 6

Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Leu Lys Asn
            20                  25                  30

Asn Gly Asn Thr Phe Leu His Trp Tyr Leu Gln Lys Ser Gly Gln Ser
        35                  40                  45

Pro Lys Leu Leu Ile Tyr Lys Val Ser Asn Arg Leu Ser Gly Val Pro
    50                  55                  60

Asp Arg Phe Ser Gly Ser Gly Ser Gly Thr Tyr Phe Thr Leu Lys Ile
65                  70                  75                  80

Ser Arg Val Glu Ala Glu Asp Leu Gly Val Tyr Phe Cys Ser Gln Ser
                85                  90                  95

Thr His Ile Pro Tyr Thr Phe Gly Gly Gly Thr Lys Leu Glu Ile Lys
            100                 105                 110

<210> SEQ ID NO 7
<211> LENGTH: 119
<212> TYPE: PRT
<213> ORGANISM: Artificial Sequence
<220> FEATURE:
<223> OTHER INFORMATION: HCVR

<400> SEQUENCE: 7

Glu Val Lys Leu Val Glu Ser Gly Gly Gly Leu Val Leu Pro Gly Asp
1               5                   10                  15

Ser Leu Arg Leu Ser Cys Ala Thr Ser Glu Phe Thr Phe Thr Asp Tyr
            20                  25                  30

Tyr Met Thr Trp Val Arg Gln Pro Pro Arg Lys Ala Leu Glu Trp Leu
        35                  40                  45

Gly Phe Ile Arg Asn Arg Ala Asn Gly Tyr Thr Thr Glu Tyr Asn Pro
    50                  55                  60

Ser Val Lys Gly Arg Phe Thr Ile Ser Arg Asp Asn Ser Gln Ser Ile
65                  70                  75                  80

Leu Tyr Leu Gln Met Asn Thr Leu Arg Thr Glu Asp Ser Ala Thr Tyr
                85                  90                  95

Tyr Cys Ala Arg Val Ser Asn Trp Ala Phe Asp Tyr Trp Gly Gln Gly
            100                 105                 110

Thr Thr Leu Thr Val Ser Ser
        115

<210> SEQ ID NO 8
<211> LENGTH: 107
<212> TYPE: PRT
<213> ORGANISM: Homo sapiens

<400> SEQUENCE: 8

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80
```

Lys His Lys Val Tyr Ala Cys Glu Val Thr His Gln Gly Leu Ser Ser
            85                  90                  95

Pro Val Thr Lys Ser Phe Asn Arg Gly Glu Cys
            100                 105

<210> SEQ ID NO 9
<211> LENGTH: 219
<212> TYPE: PRT
<213> ORGANISM: Mus musculus

<400> SEQUENCE: 9

Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Leu Lys Asn
            20                  25                  30

Asn Gly Asn Thr Phe Leu His Trp Tyr Leu Gln Lys Ser Gly Gln Ser
        35                  40                  45

Pro Lys Leu Leu Ile Tyr Lys Val Ser Asn Arg Leu Ser Gly Val Pro
    50                  55                  60

Asp Arg Phe Ser Gly Ser Gly Ser Gly Thr Tyr Phe Thr Leu Lys Ile
65                  70                  75                  80

Ser Arg Val Glu Ala Glu Asp Leu Gly Val Tyr Phe Cys Ser Gln Ser
                85                  90                  95

Thr His Ile Pro Tyr Thr Phe Gly Gly Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 10
<211> LENGTH: 217
<212> TYPE: PRT
<213> ORGANISM: Homo sapiens

<400> SEQUENCE: 10

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

```
Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Glu Glu Met
        115                 120                 125

Thr Lys Asn Gln Val Ser Leu Thr Cys Leu Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Tyr Ser Lys Leu Thr Val Asp Lys Ser Arg Trp Gln Gln Gly Asn Val
            180                 185                 190

Phe Ser Cys Ser Val Met His Glu Ala Leu His Asn His Tyr Thr Gln
        195                 200                 205

Lys Ser Leu Ser Leu Ser Pro Gly Lys
    210                 215

<210> SEQ ID NO 11
<211> LENGTH: 98
<212> TYPE: PRT
<213> ORGANISM: Artificial Sequence
<220> FEATURE:
<223> OTHER INFORMATION: mutated human CH1 gamma1

<400> SEQUENCE: 11

Ala Ser Thr Lys Gly Pro Ser Val Phe Pro Leu Ala Pro Cys Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val

<210> SEQ ID NO 12
<211> LENGTH: 98
<212> TYPE: PRT
<213> ORGANISM: Homo sapiens

<400> SEQUENCE: 12

Ala Ser Thr Lys Gly Pro Ser Val Phe Pro Leu Ala Pro Cys Ser Arg
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80
```

Tyr Thr Cys Asn Val Asn His Lys Pro Ser Asn Thr Lys Val Asp Lys
                85                  90                  95

Arg Val

<210> SEQ ID NO 13
<211> LENGTH: 15
<212> TYPE: PRT
<213> ORGANISM: Homo sapiens

<400> SEQUENCE: 13

Glu Pro Lys Ser Cys Asp Lys Thr His Thr Cys Pro Pro Cys Pro
1               5                   10                  15

<210> SEQ ID NO 14
<211> LENGTH: 15
<212> TYPE: PRT
<213> ORGANISM: Artificial Sequence
<220> FEATURE:
<223> OTHER INFORMATION: mutated hinge domain

<400> SEQUENCE: 14

Glu Pro Lys Ser Ser Asp Lys Thr His Thr Cys Pro Pro Cys Pro
1               5                   10                  15

<210> SEQ ID NO 15
<211> LENGTH: 62
<212> TYPE: PRT
<213> ORGANISM: Homo sapiens

<400> SEQUENCE: 15

Glu Leu Lys Thr Pro Leu Gly Asp Thr Thr His Thr Cys Pro Arg Cys
1               5                   10                  15

Pro Glu Pro Lys Ser Cys Asp Thr Pro Pro Pro Cys Pro Arg Cys Pro
                20                  25                  30

Glu Pro Lys Ser Cys Asp Thr Pro Pro Pro Cys Pro Arg Cys Pro Glu
            35                  40                  45

Pro Lys Ser Cys Asp Thr Pro Pro Pro Cys Pro Arg Cys Pro
        50                  55                  60

<210> SEQ ID NO 16
<211> LENGTH: 47
<212> TYPE: PRT
<213> ORGANISM: Artificial Sequence
<220> FEATURE:
<223> OTHER INFORMATION: mutated hinge domain

<400> SEQUENCE: 16

Glu Leu Lys Thr Pro Leu Gly Asp Thr Thr His Thr Cys Pro Arg Cys
1               5                   10                  15

Pro Glu Pro Lys Ser Cys Asp Thr Pro Pro Pro Cys Pro Arg Cys Pro
                20                  25                  30

Glu Pro Lys Ser Cys Asp Thr Pro Pro Pro Cys Pro Arg Cys Pro
            35                  40                  45

<210> SEQ ID NO 17
<211> LENGTH: 32
<212> TYPE: PRT
<213> ORGANISM: Artificial Sequence
<220> FEATURE:
<223> OTHER INFORMATION: mutated hinge domain

```
<400> SEQUENCE: 17

Glu Leu Lys Thr Pro Leu Gly Asp Thr Thr His Thr Cys Pro Arg Cys
1               5                   10                  15

Pro Glu Pro Lys Ser Cys Asp Thr Pro Pro Cys Pro Arg Cys Pro
            20                  25                  30

<210> SEQ ID NO 18
<211> LENGTH: 15
<212> TYPE: PRT
<213> ORGANISM: Artificial Sequence
<220> FEATURE:
<223> OTHER INFORMATION: mutated hinge domain

<400> SEQUENCE: 18

Glu Pro Lys Ser Cys Asp Thr Pro Pro Cys Pro Arg Cys Pro
1               5                   10                  15

<210> SEQ ID NO 19
<211> LENGTH: 17
<212> TYPE: PRT
<213> ORGANISM: Artificial Sequence
<220> FEATURE:
<223> OTHER INFORMATION: mutated hinge domain

<400> SEQUENCE: 19

Glu Leu Lys Thr Pro Leu Gly Asp Thr Thr His Thr Cys Pro Arg Cys
1               5                   10                  15

Pro

<210> SEQ ID NO 20
<211> LENGTH: 121
<212> TYPE: PRT
<213> ORGANISM: Artificial Sequence
<220> FEATURE:
<223> OTHER INFORMATION: Ab 301.14a

<400> SEQUENCE: 20

Ala Ser Thr Lys Gly Pro Ser Val Phe Pro Leu Ala Pro Cys Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro
        115                 120

<210> SEQ ID NO 21
<211> LENGTH: 121
<212> TYPE: PRT
<213> ORGANISM: Artificial Sequence
<220> FEATURE:
<223> OTHER INFORMATION: Ab 301.14b
```

<400> SEQUENCE: 21

Ala Ser Thr Lys Gly Pro Ser Val Phe Pro Leu Ala Pro Cys Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Ser Asp Lys Thr His Thr Cys Pro Pro Cys
            100                 105                 110

Pro Ala Pro Glu Leu Leu Gly Gly Pro
            115                 120

<210> SEQ ID NO 22
<211> LENGTH: 121
<212> TYPE: PRT
<213> ORGANISM: Artificial Sequence
<220> FEATURE:
<223> OTHER INFORMATION: Ab 301.15

<400> SEQUENCE: 22

Ala Ser Thr Lys Gly Pro Ser Val Phe Pro Leu Ala Pro Cys Ser Arg
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Thr Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro
            115                 120

<210> SEQ ID NO 23
<211> LENGTH: 168
<212> TYPE: PRT
<213> ORGANISM: Artificial Sequence
<220> FEATURE:
<223> OTHER INFORMATION: Ab 301.16

<400> SEQUENCE: 23

Ala Ser Thr Lys Gly Pro Ser Val Phe Pro Leu Ala Pro Cys Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

```
Gly Val His Thr Phe Pro Ala Val Leu Gln Ser Ser Gly Leu Tyr Ser
            50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                    85                  90                  95

Lys Val Glu Leu Lys Thr Pro Leu Gly Asp Thr Thr His Thr Cys Pro
                100                 105                 110

Arg Cys Pro Glu Pro Lys Ser Cys Asp Thr Pro Pro Cys Pro Arg
            115                 120                 125

Cys Pro Glu Pro Lys Ser Cys Asp Thr Pro Pro Cys Pro Arg Cys
            130                 135                 140

Pro Glu Pro Lys Ser Cys Asp Thr Pro Pro Cys Pro Arg Cys Pro
145                 150                 155                 160

Ala Pro Glu Leu Leu Gly Gly Pro
                165
```

<210> SEQ ID NO 24
<211> LENGTH: 168
<212> TYPE: PRT
<213> ORGANISM: Artificial Sequence
<220> FEATURE:
<223> OTHER INFORMATION: Ab 301.17

<400> SEQUENCE: 24

```
Ala Ser Thr Lys Gly Pro Ser Val Phe Pro Leu Ala Pro Cys Ser Arg
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Leu Gly Thr Gln Thr
65                  70                  75                  80

Tyr Thr Cys Asn Val Asn His Lys Pro Ser Asn Thr Lys Val Asp Lys
                    85                  90                  95

Arg Val Glu Leu Lys Thr Pro Leu Gly Asp Thr Thr His Thr Cys Pro
                100                 105                 110

Arg Cys Pro Glu Pro Lys Ser Cys Asp Thr Pro Pro Cys Pro Arg
            115                 120                 125

Cys Pro Glu Pro Lys Ser Cys Asp Thr Pro Pro Cys Pro Arg Cys
            130                 135                 140

Pro Glu Pro Lys Ser Cys Asp Thr Pro Pro Cys Pro Arg Cys Pro
145                 150                 155                 160

Ala Pro Glu Leu Leu Gly Gly Pro
                165
```

<210> SEQ ID NO 25
<211> LENGTH: 123
<212> TYPE: PRT
<213> ORGANISM: Artificial Sequence
<220> FEATURE:
<223> OTHER INFORMATION: Ab 301.18

```
<400> SEQUENCE: 25

Ala Ser Thr Lys Gly Pro Ser Val Phe Pro Leu Ala Pro Cys Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Leu Lys Thr Pro Leu Gly Asp Thr Thr His Thr Cys Pro
            100                 105                 110

Arg Cys Pro Ala Pro Glu Leu Leu Gly Gly Pro
        115                 120

<210> SEQ ID NO 26
<211> LENGTH: 123
<212> TYPE: PRT
<213> ORGANISM: Artificial Sequence
<220> FEATURE:
<223> OTHER INFORMATION: Ab 301.19

<400> SEQUENCE: 26

Ala Ser Thr Lys Gly Pro Ser Val Phe Pro Leu Ala Pro Cys Ser Arg
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Thr Cys Asn Val Asn His Lys Pro Ser Asn Thr Lys Val Asp Lys
                85                  90                  95

Arg Val Glu Leu Lys Thr Pro Leu Gly Asp Thr Thr His Thr Cys Pro
            100                 105                 110

Arg Cys Pro Ala Pro Glu Leu Leu Gly Gly Pro
        115                 120

<210> SEQ ID NO 27
<211> LENGTH: 219
<212> TYPE: PRT
<213> ORGANISM: Artificial Sequence
<220> FEATURE:
<223> OTHER INFORMATION: Chimeric light chain

<400> SEQUENCE: 27

Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Leu Lys Asn
            20                  25                  30

Asn Gly Asn Thr Phe Leu His Trp Tyr Leu Gln Lys Ser Gly Gln Ser
        35                  40                  45
```

Pro Lys Leu Leu Ile Tyr Lys Val Ser Asn Arg Leu Ser Gly Val Pro
 50                  55                  60

Asp Arg Phe Ser Gly Ser Gly Ser Gly Thr Tyr Phe Thr Leu Lys Ile
 65                  70                  75                  80

Ser Arg Val Glu Ala Glu Asp Leu Gly Val Tyr Phe Cys Ser Gln Ser
                 85                  90                  95

Thr His Ile Pro Tyr Thr Phe Gly Gly Gly Thr Lys Leu Glu Ile Lys
                100                 105                 110

Arg Thr Val Ala Ala Pro Ser Val Phe Ile Phe Pro Pro Ser Asp Glu
            115                 120                 125

Gln Leu Lys Ser Gly Thr Ala Ser Val Val Cys Leu Leu Asn Asn Phe
130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
                180                 185                 190

Lys His Lys Val Tyr Ala Cys Glu Val Thr His Gln Gly Leu Ser Ser
            195                 200                 205

Pro Val Thr Lys Ser Phe Asn Arg Gly Glu Cys
210                 215

<210> SEQ ID NO 28
<211> LENGTH: 449
<212> TYPE: PRT
<213> ORGANISM: Artificial Sequence
<220> FEATURE:
<223> OTHER INFORMATION: Chimerized heavy chain

<400> SEQUENCE: 28

Glu Val Lys Leu Val Glu Ser Gly Gly Gly Leu Val Leu Pro Gly Asp
 1               5                  10                  15

Ser Leu Arg Leu Ser Cys Ala Thr Ser Glu Phe Thr Phe Thr Asp Tyr
                 20                  25                  30

Tyr Met Thr Trp Val Arg Gln Pro Pro Arg Lys Ala Leu Glu Trp Leu
             35                  40                  45

Gly Phe Ile Arg Asn Arg Ala Asn Gly Tyr Thr Thr Glu Tyr Asn Pro
 50                  55                  60

Ser Val Lys Gly Arg Phe Thr Ile Ser Arg Asp Asn Ser Gln Ser Ile
 65                  70                  75                  80

Leu Tyr Leu Gln Met Asn Thr Leu Arg Thr Glu Asp Ser Ala Thr Tyr
                 85                  90                  95

Tyr Cys Ala Arg Val Ser Asn Trp Ala Phe Asp Tyr Trp Gly Gln Gly
                100                 105                 110

Thr Thr Leu Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
                180                 185                 190

```
Ser Ser Leu Gly Thr Gln Thr Tyr Ile Cys Asn Val Asn His Lys Pro
            195                 200                 205

Ser Asn Thr Lys Val Asp Lys Lys Val Glu Pro Lys Ser Cys Asp Lys
        210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
                260                 265                 270

Pro Glu Val Lys Phe Asn Trp Tyr Val Asp Gly Val Glu Val His Asn
            275                 280                 285

Ala Lys Thr Lys Pro Arg Glu Glu Gln Tyr Asn Ser Thr Tyr Arg Val
        290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys

<210> SEQ ID NO 29
<211> LENGTH: 98
<212> TYPE: PRT
<213> ORGANISM: Artificial Sequence
<220> FEATURE:
<223> OTHER INFORMATION: wild type human CH1 gamma1

<400> SEQUENCE: 29

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val
```

```
<210> SEQ ID NO 30
<211> LENGTH: 98
<212> TYPE: PRT
<213> ORGANISM: Artificial Sequence
<220> FEATURE:
<223> OTHER INFORMATION: mutated human CH1 gamma1

<400> SEQUENCE: 30

Ala Ser Thr Lys Gly Pro Ser Val Phe Pro Leu Ala Pro Ser Cys Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val

<210> SEQ ID NO 31
<211> LENGTH: 98
<212> TYPE: PRT
<213> ORGANISM: Artificial Sequence
<220> FEATURE:
<223> OTHER INFORMATION: human CH1 gamma 2

<400> SEQUENCE: 31

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val

<210> SEQ ID NO 32
<211> LENGTH: 98
<212> TYPE: PRT
<213> ORGANISM: Artificial Sequence
<220> FEATURE:
<223> OTHER INFORMATION: human CH1 gamma4

<400> SEQUENCE: 32

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45
```

```
Gly Val His Thr Phe Pro Ala Val Leu Gln Ser Ser Gly Leu Tyr Ser
 50                  55                  60

Leu Ser Ser Val Val Thr Val Pro Ser Ser Leu Gly Thr Lys Thr
 65                  70                  75                  80

Tyr Thr Cys Asn Val Asp His Lys Pro Ser Asn Thr Lys Val Asp Lys
                 85                  90                  95

Arg Val

<210> SEQ ID NO 33
<211> LENGTH: 113
<212> TYPE: PRT
<213> ORGANISM: Artificial Sequence
<220> FEATURE:
<223> OTHER INFORMATION: Murine IgG3 and inverse mutant CH1 and Hinge
      sequence

<400> SEQUENCE: 33

Ala Thr Thr Thr Ala Pro Ser Val Tyr Pro Leu Val Pro Gly Cys Ser
 1               5                  10                  15

Asp Thr Ser Gly Ser Ser Val Thr Leu Gly Cys Leu Val Lys Gly Tyr
                 20                  25                  30

Phe Pro Glu Pro Val Thr Val Lys Trp Asn Tyr Gly Ala Leu Ser Ser
             35                  40                  45

Gly Val Arg Thr Val Ser Ser Val Leu Gln Ser Gly Phe Tyr Ser Leu
 50                  55                  60

Ser Ser Leu Val Thr Val Pro Ser Ser Thr Trp Pro Ser Gln Thr Val
 65                  70                  75                  80

Ile Cys Asn Val Ala His Pro Ala Ser Lys Thr Glu Leu Ile Lys Arg
                 85                  90                  95

Ile Glu Pro Arg Ile Pro Lys Pro Cys Thr Pro Pro Gly Ser Ser Cys
                100                 105                 110

Pro

<210> SEQ ID NO 34
<211> LENGTH: 113
<212> TYPE: PRT
<213> ORGANISM: Artificial Sequence
<220> FEATURE:
<223> OTHER INFORMATION: Ab 301.15b

<400> SEQUENCE: 34

Ala Ser Thr Lys Gly Pro Ser Val Phe Pro Leu Ala Pro Cys Ser Arg
 1               5                  10                  15

Ser Thr Ser Gly Gly Thr Ala Ala Leu Gly Cys Leu Val Lys Asp Tyr
                 20                  25                  30

Phe Pro Glu Pro Val Thr Val Ser Trp Asn Ser Gly Ala Leu Thr Ser
             35                  40                  45

Gly Val His Thr Phe Pro Ala Val Leu Gln Ser Ser Gly Leu Tyr Ser
 50                  55                  60

Leu Ser Ser Val Val Thr Val Pro Ser Ser Leu Gly Thr Gln Thr
 65                  70                  75                  80

Tyr Thr Cys Asn Val Asn His Lys Pro Ser Asn Thr Lys Val Asp Lys
                 85                  90                  95

Arg Val Glu Pro Lys Ser Ser Asp Lys Thr His Thr Cys Pro Pro Cys
                100                 105                 110

Pro
```